US005765740A

United States Patent [19]
Ferguson

[11] Patent Number: 5,765,740
[45] Date of Patent: Jun. 16, 1998

[54] SUTURE-MATERIAL-DISPENSER SYSTEM FOR SUTURE MATERIAL

[76] Inventor: Patrick J. Ferguson, 315 NE. Laurelhurst, Portland, Oreg. 97232

[21] Appl. No.: 497,432

[22] Filed: Jun. 30, 1995

Related U.S. Application Data

[63] Continuation-in-part of Ser. No. 175,964, Dec. 30, 1993, abandoned.

[51] Int. Cl.⁶ .............................. A61B 17/06; B26F 3/02
[52] U.S. Cl. .............................. 225/46; 225/39; 225/40; 225/56; 225/82; 225/90; 206/63.3
[58] Field of Search ........................ 225/39, 40, 46, 225/56, 82, 90; 83/175; 206/63.3, 63.5

[56] References Cited

U.S. PATENT DOCUMENTS

| | | |
|---|---|---|
| 2,128,701 | 8/1938 | Gelinsky . |
| 2,808,927 | 10/1957 | Utley et al. . |
| 3,728,839 | 4/1973 | Glick . |
| 3,815,315 | 6/1974 | Glick . |
| 3,995,631 | 12/1976 | Higuchi et al. .......................... 128/260 |
| 4,034,756 | 7/1977 | Higuchi et al. .......................... 128/260 |
| 4,499,930 | 2/1985 | Walters ....................................... 141/8 |
| 4,566,606 | 1/1986 | Kling . |
| 4,606,134 | 8/1986 | Flick . |
| 4,730,726 | 3/1988 | Holzwarth . |
| 4,903,826 | 2/1990 | Pearce . |
| 4,925,073 | 5/1990 | Tarrson et al. . |
| 5,012,678 | 5/1991 | Buchanan ................................... 73/738 |
| 5,022,577 | 6/1991 | Fike . |
| 5,065,861 | 11/1991 | Greene et al. . |
| 5,086,914 | 2/1992 | Mish et al. . |
| 5,133,747 | 7/1992 | Feaster . |
| 5,160,077 | 11/1992 | Sticklin . |
| 5,263,585 | 11/1993 | Lawhon et al. . |
| 5,263,621 | 11/1993 | Bedi . |
| 5,280,741 | 1/1994 | Bell et al. . |
| 5,501,674 | 3/1996 | Trombley, III et al. ................ 604/247 |

Primary Examiner—Eugenia Jones
Assistant Examiner—Charles Goodman
Attorney, Agent, or Firm—Kolisch, Hartwell, Dickinson, McCormack & Heuser

[57] ABSTRACT

A suture-material-dispenser system for a supply of dry or wet suture material includes the supply of such material and a housing which defines a cavity for containing the supply. The housing includes a top region that has an opening formed in it, and a bottom region with a semi-circular bearing positioned in it. A reel fits within the cavity on the bearing, and has wound on it the supply. An anti-contaminant, flip-top cover is pivotably attached to the top region, and is constructed for releasable closure over the top region substantially to prevent contaminants from entering the cavity. A gas-permeable, resilient member is also included and has a body that fits sealingly within the opening, which body has formed in it a suture-material-dispensing port to allow dispensing of suture material therethrough. The body is preferably formed from a substance with a hardness in the range of about 40–80 on a Shore A durometer. An on-board cutter is also attached to the housing adjacent the resilient member for allowing the user to cut a desired dispensed amount of material from such supply. The cover may also include a downwardly extending, elongate pressure applicator with a bottom surface that presses against the resilient member adjacent the port when the cover is closed over the top region. Preferably, the resilient member is formed from a material that is ethylene-oxide-gas permeable, such as liquid-injection-molded silicone.

31 Claims, 5 Drawing Sheets

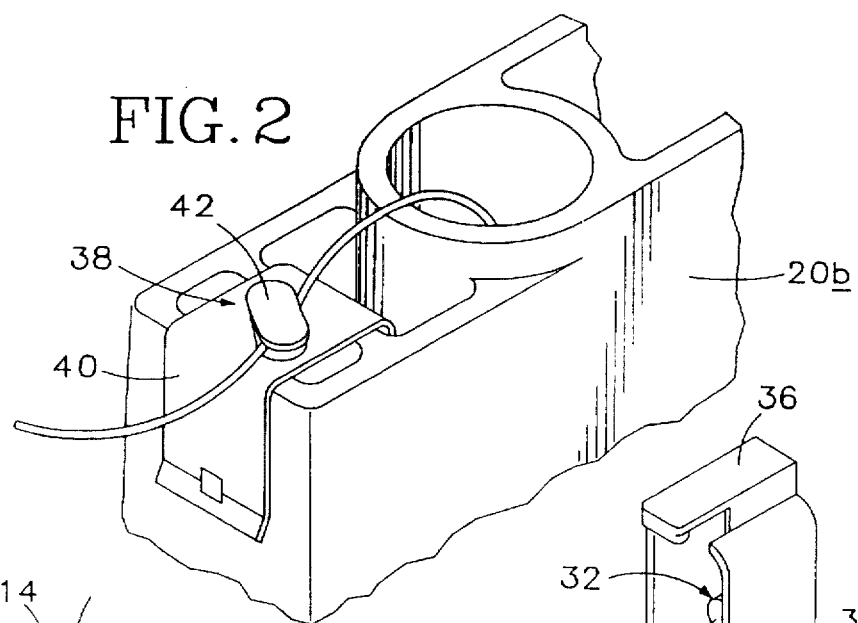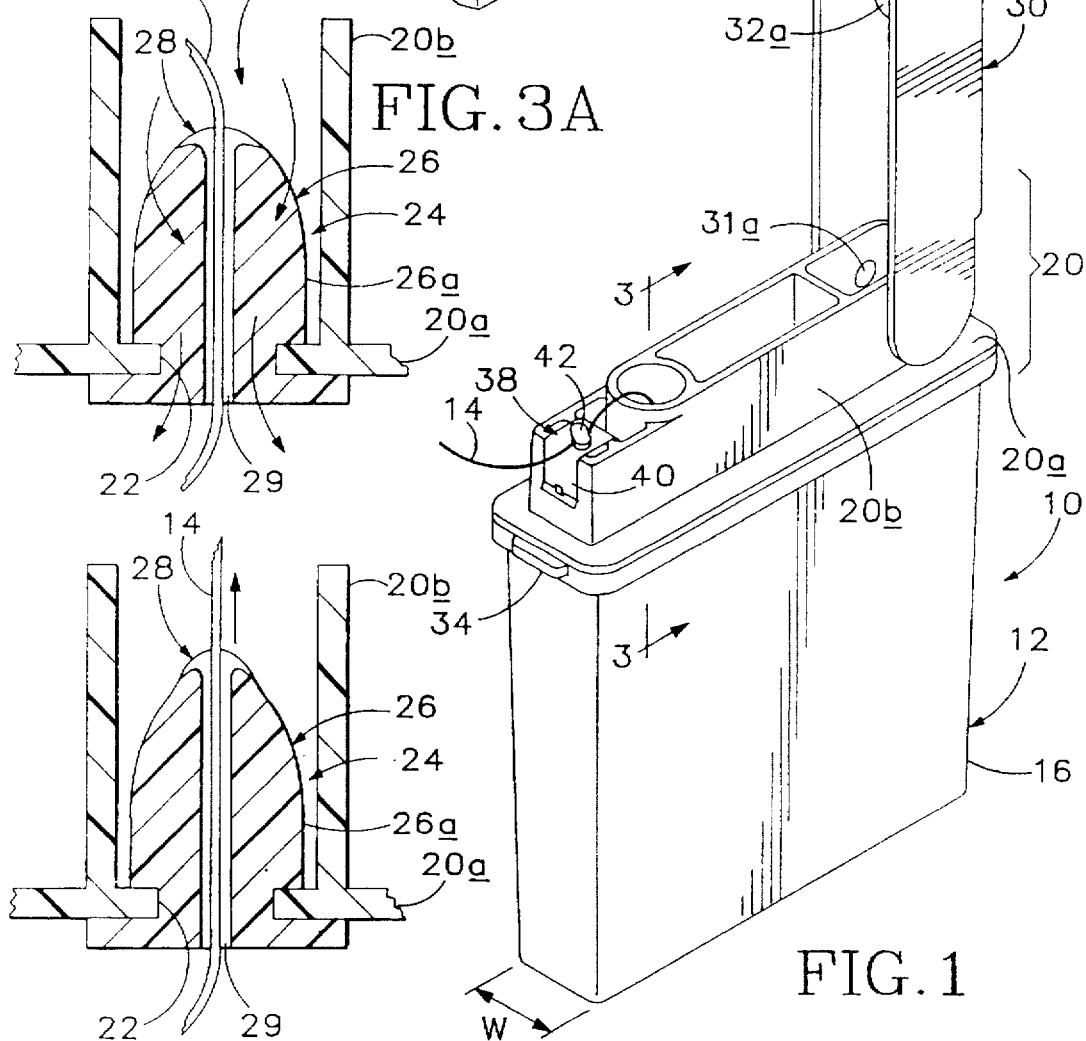

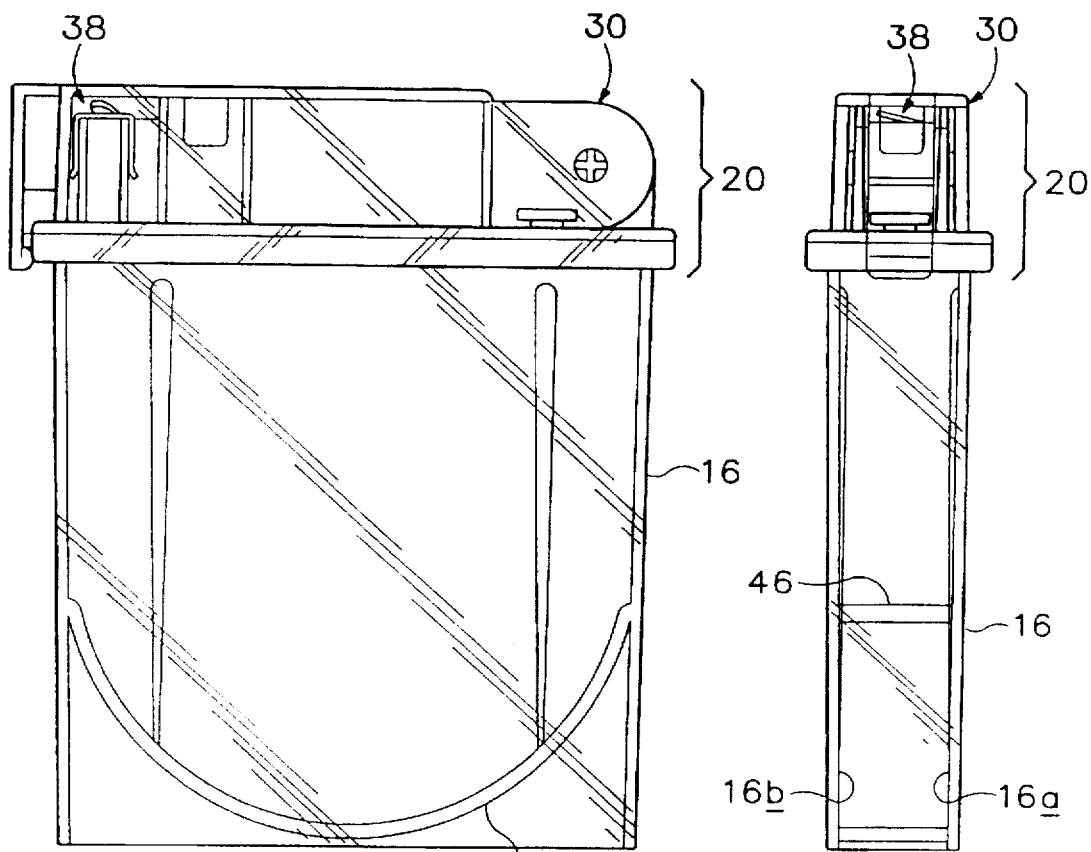
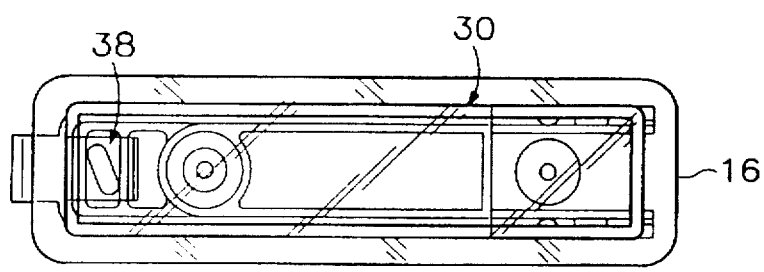
FIG. 9   FIG. 10
FIG. 11

SUTURE-MATERIAL-DISPENSER SYSTEM FOR SUTURE MATERIAL

CROSS REFERENCE TO RELATED APPLICATION

This is a continuation-in-part of application Ser. No. 08/175,964 filed Dec. 30, 1993, now abandoned.

BACKGROUND AND SUMMARY OF THE INVENTION

The present invention relates generally to suture-material dispensers. More particularly, the invention concerns a novel suture-material-dispenser system for dry or wet suture material.

Generally speaking, the present invention is usable for all surgical applications, but it is particularly suited for use by veterinary surgeons, as will be better understood from the description below. For that reason, the present invention will be described in the context of use by veterinary surgeons. As used below, the word sterile or sterilization means that degree of sterileness which is found acceptable in veterinary surgery.

Conventional suture dispensers are well known. Such dispensers are characterized by having relatively large dimensions, and are constructed for holding wet suture material, one type of conventional suture material that is packaged in an alcohol-based solution. The other type is dry suture material and it will be discussed below in connection with the present invention.

To sterilize wet suture material in conventional, so-called "wet-pack" dispensers, an extreme procedure must be followed which involves irradiating the filled dispenser with gamma-ray radiation. Such a procedure is extreme because it tends to modify or adversely affect the molecular structure of the suture material. After irradiation, suture material from conventional "wet packs" tends to become weaker and stiffer, which makes it more difficult for a surgeon to work with. The integrity of the material is also compromised. Such an extreme sterilization procedure is required because there is no other known way to sterilize wet suture material.

Conventional dispensers, or "wet packs", are also disfavored because the wet suture material is messy, relatively heavy and flammable.

Conventional dispensers also require a two-handed operation for dispensing and cutting suture material. Essentially, the user, such as a surgeon or other surgical health care professional, holds the dispenser while removing a desired amount of suture material from the supply contained within the dispenser. Next, the user grasps a cutting instrument such as a pair of scissors and cuts the desired amount from the supply.

With respect to wet packs, conventional dispensers require about 2–4 ounces of sterilization liquid such as a solution of 90% isopropyl alcohol and 10% water. The current liquid-volume requirement of conventional dispensers results in an undesirably heavy package which is costly to ship or transport due to weight and hazardous material charges.

None of the conventional dispensers is designed for one-handed dispensing and cutting operation, and none is constructed for holding dry suture material.

Accordingly, it is a principal object of the present invention to provide a suture-material-dispenser system which overcomes the drawbacks of prior art systems.

Another object is to provide such a system that can hold and dispense dry suture material, and allow that material to be sterilized using a substantially dry, gas sterilization procedure.

Yet another object is to provide such a system that allows for a one-handed dispensing and cutting operation.

Another important object of the invention is to provide such a system with a flip-top for promoting one-hand operation of opening and closing.

Still another object is to provide such a system that is sized for easy storage and transport.

Yet another object is to provide such a system that is usable for wet or dry suture material.

Still another object is to provide such a system for holding wet suture material and an optimal amount of sterilization fluid.

It is also an object of the invention to provide such a system that can be cost-effectively manufactured.

In brief summary, one aspect of the invention includes a suture-material-dispenser system for a supply of dry or wet suture material with a housing and a gas-permeable, resilient member. The housing defines a cavity for containing a supply of such material, and it includes a top region that has an opening formed in it. The gas-permeable, resilient member has a body that fits sealingly within the opening, and the body has formed in it a suture-material-dispensing port for allowing suture material to be dispensed therethrough. The port is preferably formed as a slit with a length of about 2–6 mm.

The body assumes a pre-dispense condition and a dispense condition, and the body is formed from a substance with a memory characteristic allowing that section of the body adjacent the port to deform when the body is in the dispense condition, thus to minimize degradation of suture material during dispensing operation. The memory characteristic also allows the body to return substantially to its undeformed state when the body is in its pre-dispense condition, thus to seal substantially the cavity from contaminant.

The invention preferably also includes the following other features. An anti-contaminant, flip-top cover is pivotably attached to the top region, and is constructed for releasable closure over the top region substantially to prevent contaminants from entering the cavity. The cover also includes a downwardly extending, elongate pressure applicator with a bottom surface that presses against the resilient member adjacent the port when the cover is closed over the top region. The top region also includes a lip that extends outwardly from the housing, and the cover includes a downwardly extending expanse that is engageable with lip to obtain such releasable closure.

An on-board cutter is preferably attached to the housing adjacent the resilient member for allowing the user to cut a desired dispensed amount of material from such supply. The resilient member is preferably formed from a material such as liquid-injection-molded silicone, which material is ethylene-oxide-gas permeable, and has the above-described memory characteristic. The resilient member is also preferably formed from a material with a hardness in the range of about 40–80 on a Shore A durometer.

Another aspect of the invention includes the above suture-material-dispenser system and the supply of dry suture material. That version of the invention also includes a reel fittable within the cavity, and having wound on it the supply. The housing also includes a bottom region and a semicircular bearing positioned in the bottom region for supporting the reel.

Yet another aspect of the invention includes the above suture-material-dispenser system and a supply of wet suture material. The wet suture material is wound on a reel fittable within the cavity, and the wet suture material is wetted by an amount of sterilization liquid. The reel is sized to optimize the quantity of sterilization liquid disposed within the cavity.

These and other objects and advantages of the invention will be more clearly understood from a consideration of the accompanying drawings and the following description of the preferred embodiment.

BRIEF DESCRIPTION OF THE DRAWINGS

FIG. 1 is an isometric view showing the preferred embodiment of the suture dispenser system of the present invention with its cover being pivoted to an open position allowing access to dry suture material contained in the system.

FIG. 2 is an enlarged, fragmentary, view of a top section of the system shown in FIG. 1 which illustrates the dispensing and cutting operations achievable using the invention.

FIG. 3A is an enlarged, fragmentary, cross-sectional view through line 3—3 of FIG. 1.

FIG. 3B is an enlarged, fragmentary, cross-sectional view like FIG. 3A, only showing in an exaggerated way how the resilient member of the present invention deforms during dispensing.

FIG. 9 is a side view of the housing shown in FIG. 8, shown in approximately actual size;

FIG. 10 is an end view of the housing shown in FIG. 9, shown on about the same scale as FIG. 9; and FIG. 11 is a top view of the housing shown in FIG. 9, shown on about the same scale as FIG. 9.

DETAILED DESCRIPTION OF THE PREFERRED EMBODIMENT

FIG. 1 depicts an isometric view of the suture dispenser system of the present invention, being made in accordance with its preferred embodiment and indicated at 10. The preferred embodiment includes the to-be-described dispenser 12 and dry-suture material ("DSM") 14. DSM 14 can be obtained from CP Medical Of Portland, Oreg. and suitable versions of DSM 14 are sold CP Medical under the trademarks FLEX-GUT, MONOMID, and SUPRAMID.

Figure 4:
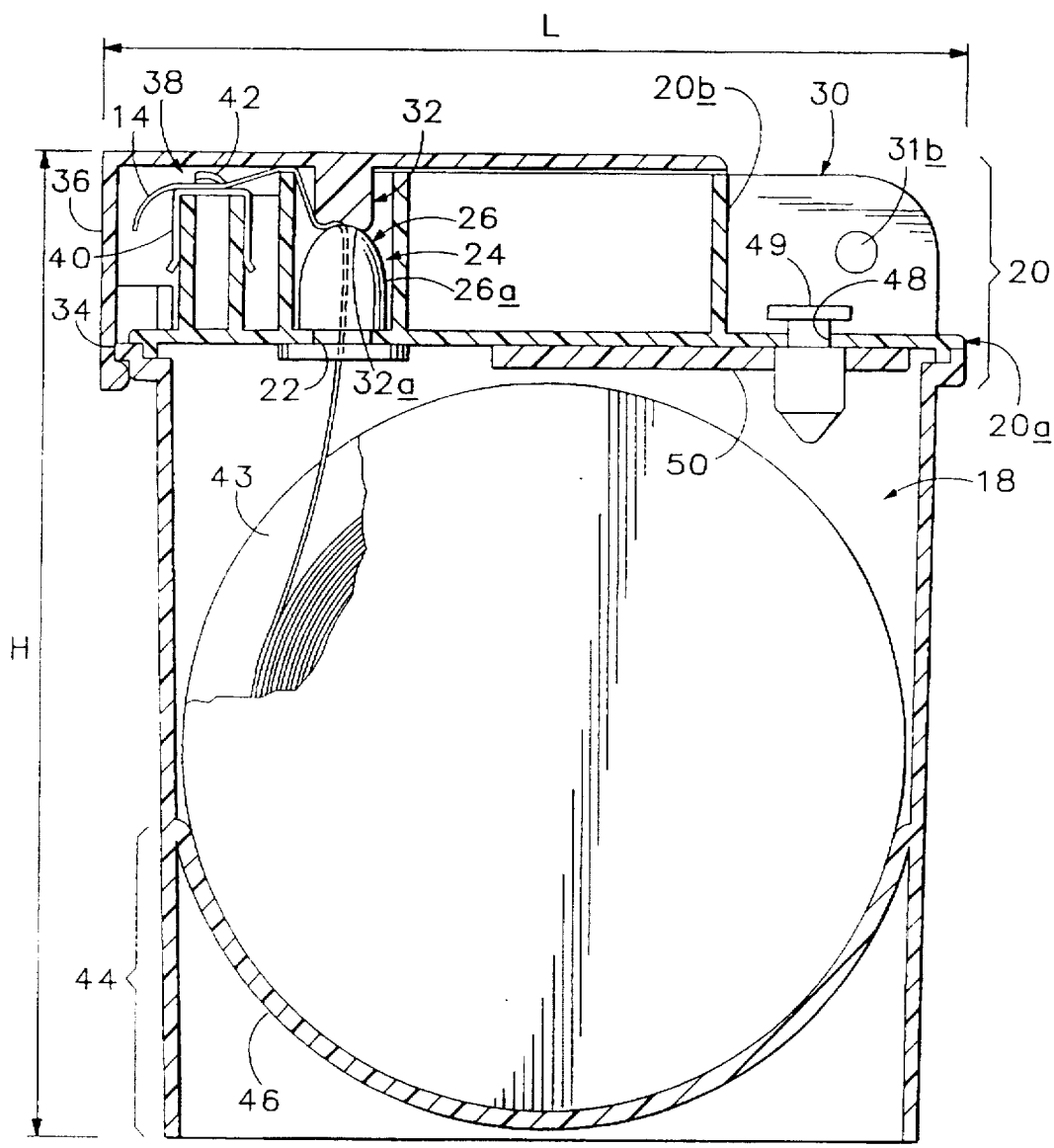
FIG. 4 is a side sectional view of the system shown in FIG. 1 after the cover is moved to a closed position.

Referring to FIGS. 1, 4 and 10, the invention includes a housing 16, preferably made from clear ABS plastic, which defines a cavity 18 (FIG. 4) for containing a supply of DSM 14. The housing includes opposing walls 16a-b (FIG.10) and a top region 20 that has an opening 22 (FIG. 4) formed in it. Fitting sealingly within opening 22 is a gas-permeable, resilient member 24 having a body 26 with a suture-material-dispensing port 28 (FIGS. 3A and 3B) for allowing DSM 14 to be dispensed through it. Top region 20 includes a plate-like member 20a which can be fastened to housing 16 using suitable means such as adhesive. All components of system 10 are preferably made of a suitable plastic, but any suitable material may be used. Top region 20 also includes a raised member 20b which is positioned fixedly and centrally of plate-like member 20a.

Referring to FIGS. 3A-3B, two conditions of body 26 will be described, a pre-dispense condition and a dispense condition. These figures will illustrate a to-be-described memory characteristic of body 26. FIG. 3B shows, in an enlarged and exaggerated way, that the portion of body 26 adjacent port 28 deforms when the body is in the dispense condition with DSM 14 being pulled out of cavity 18 (FIG. 4) in the direction of the arrow. Such deformation, combined with the to-be-described softness of body 26, tends to minimize degradation of suture material during dispensing operations.

With respect to material choice for body 26, the preferred material is liquid-injection-molded, or LIM, silicone. The material also has a hardness in the range of about 40–80 on a Shore A durometer. The material is also preferably ethylene-oxide-gas permeable to allow system 10 to be sterilized according to a to-be-described, conventional ethylene-oxide-gas sterilization procedure.

Referring back to FIG. 3A, the memory characteristic of body 26 allows the body to return substantially to its undeformed state when the body is in its pre-dispense condition as shown. The pre-dispense condition occurs when no dispensing, or pulling, force is applied to DSM 14. By returning to its undeformed state, body 26 will seal substantially cavity 18 (FIG. 4) from contaminant. Preferably, port 28 is formed as a slit, with a length of about 2–6 mm, in the top surface 26a of body 26 to maximize the capability of body 26 to seal cavity 18 from contaminant. Body 26 is shown in FIGS. 3A–3B also with a cylindrical void 29 which communicates with port 28 and cavity 18. The shape of that void is not critical however, and body 26 could also be constructed substantially hollow (undepicted) with only a suitable uniform thickness associated with its surface area.

Still referring to FIG. 3A, there is also depicted the gas-permeable nature of resilient member 24 as to-be-described sterilizing gas, shown by arrows, penetrates through body 26 into cavity 18.

Referring to FIGS. 1 and 4, system 10 also preferably includes an anti-contaminant, flip-top cover 30 which is pivotably attached to top region 20 via opposing bosses 31a–b which extend inwardly from opposing sides of the cover into suitable, corresponding holes formed in top region 20. Cover 30 is constructed for releasable closure over the top region substantially to prevent contaminants from entering the cavity. In this way the cover acts as a backup seal to the primary seal provided by body 26 as described above in connection with FIG. 3A.

Still referring to FIGS. 1 and 4, cover 30 includes a downwardly extending, elongate pressure applicator 32 with a bottom surface 32a that presses against resilient member 24 adjacent port 28 when cover 30 is closed over top region 20. Pressure applicator 32 functions as another backup seal by covering the area of top surface 26a of body 26 around port 28.

To provide releasable closure of cover 30 over top region 20, top region 20 is preferably constructed with a lip 34 that extends outwardly from housing 16, and cover 30 includes a downwardly extending expanse 36 that is engageable with lip 34 to obtain such releasable closure.

Referring to FIGS. 1–2 and 4, system 10 also preferably includes an on-board cutter 38 attached to raised member 20b of top region 20 of housing 16 adjacent resilient member 24. Cutter 38 allows the user to cut a desired dispensed amount of DSM 14 from the remaining supply of that material in cavity 18. Cutter 38 is preferably made as an elongate section 40 of a suitable metal. Section 40 is die cut to form a cutter blade 42 which is bent upwardly a suitable amount to allow DSM 14 to be fed under it and, ultimately, pulled against it to cut a desired amount of DSM 14 from the supply. Section 40 is formed as a clip to fit over a section of raised member 20b, but any suitable means of attaching cutter 38 to dispenser 12 may of course be used.

Referring to FIG. 4, system 10 also preferably includes a reel 43 fittable within cavity 18 for retaining the supply of DSM 14. To support reel 43, a bottom region 44 of housing 16 includes a semi-circular bearing 46 positioned in it. Given the below described dimensions of system 10, reel 43 is sized to hold between about 50–110 yards of DSM 14.

Referring to FIG. 4, there is shown an auxiliary opening 48 formed in top region 20 with a conventional nipple 49 sealing positioned therein. A support plate 50 is also suitably attached to the underside of plate-like member 20a for supporting nipple 49. With nipple 49, the system of the present invention can also be used with wet-suture material ("WSM"), and nipple 49 can be used as what is known as a fill hole for adding wet sterilization liquid such as the usual alcohol-based ones.

Figure 5:
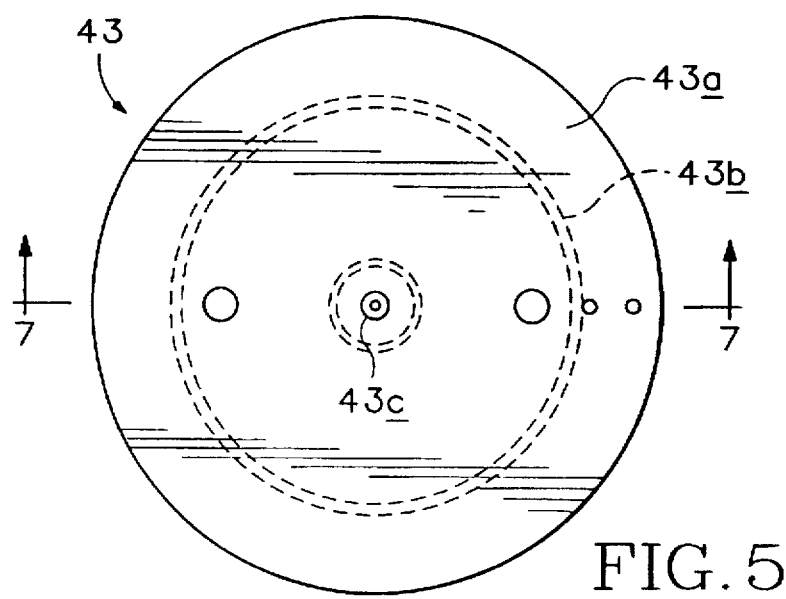
FIG. 5 is a side view of the reel shown in FIG. 4, removed from the system, shown in approximately actual size.
Figure 6:
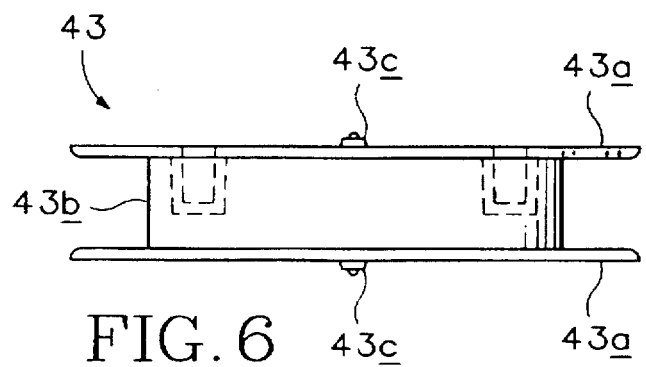
FIG. 6 is a bottom view of the reel shown in FIG. 5, on about the same scale as FIG. 5.
Figure 7:
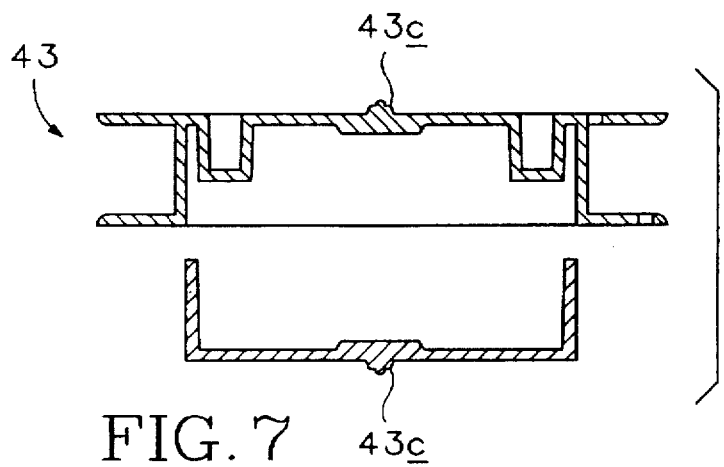
FIG. 7 is a cross-sectional view of a modified version of the reel shown in FIG. 5, taken along line 7—7 shown in FIG. 5, shown on about the same scale as FIG. 5, and shown with the reel separated into its subparts as manufactured in the preferred embodiment.
Figure 8:
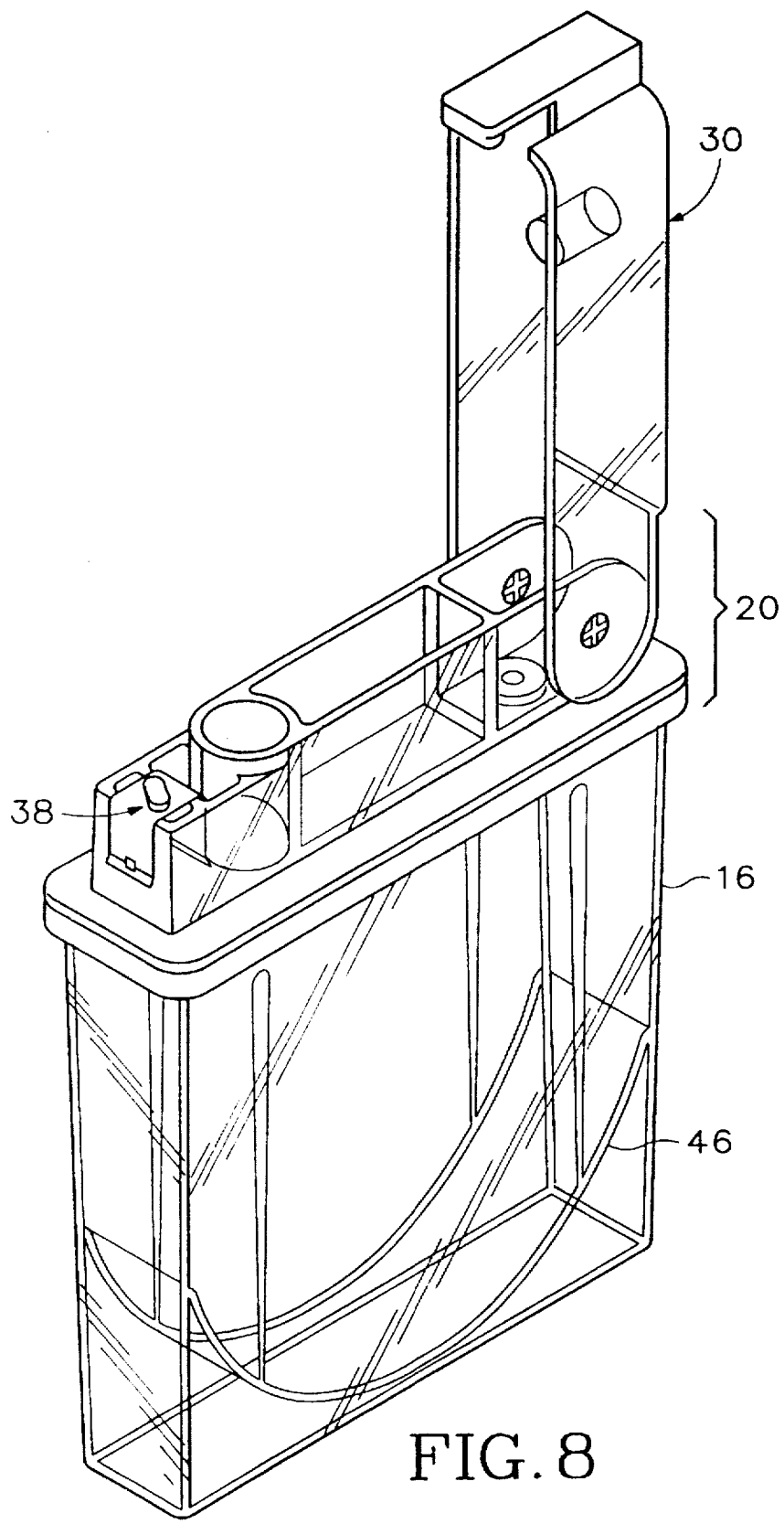
FIG. 8 is an isometric view of an alternative embodiment of the housing of the present invention, shown in a position similar to that shown in FIG. 1, and on a slightly larger scale.

Referring to FIGS. 5–7, further details of reel 43 are shown. Reel 43 is preferably made of a durable plastic material such as clear ABS plastic. Reel 43 includes opposing disks 43a, a central spool 43b, and opposing hub-like bearings 43c. Bearings 43c contact inside surfaces of walls 16a–b, and cooperate with the inside surfaces of walls 16a–b to provide bearing function to allow rotation of reel 43. In addition, bearings 43c resist compressive forces applied to walls 16a–b, such as those forces that may be applied by the user's hand when the user grasps or holds dispenser 12. By resisting those forces, bearings 43c tend to promote free rotation of reel 43 within housing 16.

Central spool 43b may be any suitable size, and preferably spool 43b is sized to hold between about 50–110 yards of wet suture material. Preferably, disks 43a have a diameter of about 3³⁄₁₆", and spool 43b has a diameter of about 2⁷⁄₁₆". With the preferred diameters, the volume of sterilization liquid required to fill the remainder of the cavity is ≦1 ounce, and preferably about 0.8–1.0 ounces.

In FIGS. 8, 9, 10 and 11, an alternative embodiment of the housing is shown, identified generally at 16. Top region 20, flip-top cover 30, cutter 38, and semi-circular bearing 46 are labeled for reference, as appropriate.

With the above construction of system 10, it is possible to sterilize it using conventional gas-sterilization procedures such as ethylene-oxide-gas sterilization performable by Dravon Medical of Portland, Oreg. Either 100% ethylene oxide or 12% formaldehyde/88% ethylene oxide can be used to perform that gas sterilization.

Operation

In use, system 10 can be held easily in the user's hand and stored in a pocket of the user's clothing. Referring to FIGS. 1 and 4, the overall dimensions of system 10 are about 4⁵⁄₁₆" high ("H")×3¹³⁄₁₆" long ("L")×⁷⁄₈" wide ("W"). From its covered position as shown in FIG. 4, the user simply presses outwardly and upwardly against the bottom of expanse 36 (i.e. the bottom as shown in FIG. 4) to disengage it from lip 34 and open cover 30. When cover 30 is in its open position (FIG. 1), the user simply pulls a desired amount of DSM 14 from housing 16 and cuts that amount from the supply of DSM 14 by feeding under cutter blade 42 and then pulling that amount against that blade.

After dispensing, the user is able to close flip-top cover 30 with the same hand being used to hold system 10 by simply pushing down on an accessible section of the cover with the thumb. With respect to later use of the section of DSM 14 that extends outwardly from resilient member 24 to cutter 38 (see FIG. 4), it will depend on the user's own sterile procedures. If sterile gloves are used when handling DSM 14, it is likely that that section is sufficiently sterile for use.

It should now be understood that the present invention meets the above objects by providing a suture-material-dispenser system which overcomes the drawbacks of prior art systems. System 10 is constructed for holding and dispensing dry suture material, and for allowing that material to be sterilized using a substantially dry, gas sterilization procedure. System 10 also includes a flip-top for promoting one-hand operation of opening and closing. Cutter 38 makes it possible to perform one-handed dispensing and cutting.

The overall dimensions of system 10 make it easy to handle, store and transport on the user's person. Because system 10 also includes nipple 49, it can be used with wet or dry suture material. Also, system 10 can be cost-effectively manufactured.

Accordingly, while a preferred embodiment of the invention has been described herein, it is appreciated that modifications are possible that are within the scope of the invention.

It is claimed and desired to secure by Letters Patent:

1. A suture-material-dispenser system for dry suture material, comprising:

a housing which defines a cavity for containing the suture material, with the housing including a top region that has an opening; and a resilient member formed from a gas-permeable material, the member having a body that fits sealingly within the opening, the body having a suture-material-dispensing port for allowing the suture material to be dispensed therethrough, the body having a pre-dispense condition and a dispense condition, and the gas-permeable material having a memory characteristic that allows the body adjacent the port to deform when the body is in the dispense condition, thus to minimize degradation of the suture material during dispensing of suture material, and the memory characteristic also allows the body to return substantially to the pre-dispense condition, thus to seal substantially the cavity from contaminant.

2. The system of claim 1 wherein an anti-contaminant, flip-top cover is pivotably attached to the top region, and is constructed for releasable closure over the top region substantially to prevent contaminants from entering the cavity.

3. The system of claim 2 wherein the cover further includes a downwardly extending, elongate pressure applicator with a bottom surface that presses against the resilient member adjacent the port when the cover is closed over the top region.

4. The system of claim 3 wherein the top region includes a lip that extends outwardly from the housing, and the cover includes a downwardly extending expanse that is engageable with the lip to obtain the releasable closure.

5. The system of claim 4 further comprising an on-board cutter attached to the housing adjacent the resilient member for allowing a user to cut a desired dispensed amount of the suture material.

6. The system of claim 2 wherein the top region includes a lip that extends outwardly from the housing, and the cover includes a downwardly extending expanse that is engageable with the lip to obtain the releasable closure.

7. The system of claim 6 further comprising an on-board cutter attached to the housing adjacent the resilient member for allowing a user to cut a desired dispensed amount of the suture material.

8. The system of claim 2 further comprising an on-board cutter attached to the housing adjacent the resilient member for allowing a user to cut a desired dispensed amount of the suture material.

9. The system of claim 3 further comprising an on-board cutter attached to the housing adjacent the resilient member for allowing a user to cut a desired dispensed amount of the suture material.

10. The system of claim 1 further comprising an on-board cutter attached to the housing adjacent the resilient member for allowing a user to cut a desired dispensed amount of the suture material.

11. The system of claim 1 wherein the material of the resilient member is that is ethylene-oxide-gas permeable.

12. The system of claim 1 wherein the body of the resilient member is formed from liquid- injection-molded silicone.

13. The system of claim 1 further comprising a supply of suture material contained in the cavity and a reel is fittable within the cavity, wherein the supply is wound onto the reel and the housing includes a bottom region and a semi-circular bearing positioned in the bottom region for supporting the reel.

14. The system of claim 1 wherein the port is formed as a slit with a length of about 2–6 mm.

15. The system of claim 1 wherein the material of the resilient member has a hardness in a range of about 40–80 on a Shore A durometer.

16. A suture-material-dispenser system for dry suture material, comprising:

a housing which defines a cavity for containing the suture material, with the housing including a top region that has an opening;

an anti-contaminant, flip-top cover pivotably attached to the top region, and being constructed for releasable closure over the top region substantially to prevent contaminants from entering the cavity;

a resilient member formed from a gas-permeable material, the resilient member having a body that fits sealingly within the opening, the body having a suture-material-dispensing port for allowing the suture material to be dispensed therethrough, and the gas-permeable material having a hardness in a range of about 40–80 on a Shore A durometer; and an on-board cutter attached to the housing adjacent the resilient member for allowing a user to cut a desired dispensed amount of the suture material.

17. The system of claim 16 wherein the cover further includes a downwardly extending, elongate pressure applicator with a bottom surface that presses against the resilient member adjacent the port when the cover is closed over the top region.

18. The system of claim 17 wherein the top region includes a lip that extends outwardly from the housing, and the cover includes a downwardly extending expanse that is engageable with the lip to obtain the releasable closure.

19. The system of claim 16 wherein the material of the resilient member is ethylene-oxide-gas permeable.

20. The system of claim 16 wherein the body of the resilient member is formed from liquid- injection-molded silicone.

21. The system of claim 16 further comprising a supply of suture material and a reel fittable within the cavity, wherein the supply is wound onto the reel and the housing includes a bottom region and a semi-circular bearing positioned in the bottom region for supporting the reel.

22. The system of claim 16 wherein the port is formed as a slit with a length of about 2–6 mm.

23. A suture-material-dispenser system, comprising:

a housing which defines a cavity, the housing including a top region that has an opening, and a bottom region with a semi-circular bearing positioned in the bottom region;

a reel fittable within the cavity on the bearing;

a supply of dry suture material wound onto the reel;

an anti-contaminant, flip-top cover pivotably attached to the top region, and being constructed for releasable closure over the top region substantially to prevent contaminants from entering the cavity;

a resilient member formed from a gas-permeable material, the resilient member having a body that fits sealingly within the opening, the body having a suture-material-dispensing slit for allowing the suture material to be dispensed therethrough, and the gas-permeable material having a hardness in a range of about 40–80 on a Shore A durometer; and an on-board cutter attached to the housing adjacent the resilient member for allowing a user to cut a desired dispensed amount of suture material from the supply.

24. The system of claim 23 wherein the cover further includes a downwardly extending, elongate pressure applicator with a bottom surface that presses against the resilient member adjacent the slit when the cover is closed over the top region.

25. The system of claim 24 wherein the top region includes a lip that extends outwardly from the housing, and the cover includes a downwardly extending expanse that is engageable with the lip to obtain the releasable closure.

26. The system of claim 25 wherein the material of the resilient member is ethylene-oxide-gas permeable.

27. The system of claim 23 wherein the body of the resilient member is formed from liquid-injection-molded silicone.

28. A suture-material-dispenser system, comprising:

a housing which defines a cavity, with the housing including a top region that has an opening, and a bottom region with a semi-circular bearing positioned in the bottom region;

a preselected volume of sterilization liquid disposable in the cavity to fill the cavity;

a reel fittable within the cavity on the bearing;

a supply of wet suture material wound onto the reel;

an anti-contaminant, flip-top cover pivotably attached to the top region, and being constructed for releasable closure over the top region substantially to prevent contaminants from entering the cavity;

a resilient member formed from a gas-permeable material, the resilient member having a body that fits sealingly within the opening, the body having a suture-materialdispensing slit for allowing the suture material to be dispensed therethrough, and the gas-permeable material having a hardness in a range of about 40–80 on a Shore A durometer; and an on-board cutter attached to the housing adjacent the resilient member for allowing a user to cut a desired dispensed amount of material from the supply.

29. The system of claim 28 wherein the cover further includes a downwardly extending, elongate pressure applicator with a bottom surface that presses against the resilient member adjacent the slit when the cover is closed over the top region.

30. The system of claim 29 wherein the top region includes a lip that extends outwardly from the housing, and the cover includes a downwardly extending expanse that is engageable with the lip to obtain the releasable closure.

31. The system of claim 28 wherein the body of the resilient member is formed from liquid-injection-molded silicone.

* * * * *